(12) United States Patent
Hagiwara et al.

(10) Patent No.: US 6,354,998 B1
(45) Date of Patent: Mar. 12, 2002

(54) BLOOD PRESSURE DETERMINING APPARATUS AND METHOD OF DETERMINING EXCITATION FREQUENCY USED IN THE SAME

(75) Inventors: Hisashi Hagiwara, Yokohama; Hiroshi Fukukita, Tokyo; Kinya Hasegawa, Sagamihara; Yushi Nishimura, Yokohama, all of (JP)

(73) Assignee: Matsushita Electric Industrial Co., Ltd. (JP)

( * ) Notice: Subject to any disclaimer, the term of this patent is extended or adjusted under 35 U.S.C. 154(b) by 34 days.

(21) Appl. No.: 09/617,133

(22) Filed: Jul. 14, 2000

(30) Foreign Application Priority Data

Sep. 27, 1999 (JP) ............................................. 11-272730

(51) Int. Cl.$^7$ ................................................. A61B 5/00
(52) U.S. Cl. ....................................... 600/485; 600/500
(58) Field of Search ................................. 600/485, 490, 600/493–6, 500

(56) References Cited

U.S. PATENT DOCUMENTS 5,590,649 A        1/1997   Caro et al.
5,791,347 A  *    8/1998   Flaherty et al. ............. 600/485
5,810,734 A  *    9/1998   Caro et al. ................... 600/485
5,830,131 A  *   11/1998   Caro et al. ................... 600/485
5,904,654 A  *    5/1999   Wohltmann et al. ........ 600/500

* cited by examiner

*Primary Examiner*—Robert L. Nasser
(74) *Attorney, Agent, or Firm*—Parkhurst & Wendell, LLP

(57) ABSTRACT

A blood pressure determining apparatus is provided which applies oscillations to the blood vessel of a subject through an exciter to determine the blood pressure based on the frequency of the oscillations propagated through the blood vessel measured by an oscillation sensor. The apparatus monitors an output of the oscillation sensor when the exciter applies no oscillation to the subject to determine the power spectrum of noise signals contained in the output and sets the frequency of oscillations to be applied to the blood vessel to any value within a band of the power spectrum in which the power of noise is small. This enables the blood pressure to be determined without influence of any electric disturbances from peripheral devices.

4 Claims, 4 Drawing Sheets

BLOOD PRESSURE DETERMINING APPARATUS AND METHOD OF DETERMINING EXCITATION FREQUENCY USED IN THE SAME

BACKGROUND OF THE INVENTION

1. Technical Field of the Invention

The present invention relates generally to a blood pressure measuring apparatus which applies weak oscillations to a blood vessel in a living body and measures and analyze the oscillations transmitted through the blood vessel to determine the blood pressure continuously, and more particularly to a blood pressure measuring apparatus designed to monitor the oscillations with high sensitivity regardless of electrical noises arising from ac power supply and/or other peripheral devices and an excitation frequency determining method used in the blood pressure measuring apparatus.

2. Background Art

U.S. Pat. No. 5,590,649 issued on Jan. 7, 1997 discloses a blood pressure determining system which performs a continuous non-invasive measurement of blood pressure. This system is designed to estimate the blood pressure by measuring the velocity of propagation of oscillations through a blood vessel based on the fact that the elasticity of the blood vessel changes with a change in blood pressure, and that a change in elasticity of the blood vessel causes the velocity of propagation of oscillations through the blood vessel to change.

FIG. 3 shows the blood pressure determining circuit as discussed above.

The exciter 2 and the oscillation sensor 4 are attached to the patient's forearm. The cuff 8 is installed around the patient's upper arm. The oscillator 3 outputs a signal of a frequency f to the exciter 2 to induce perturbations or oscillate the radial artery in the forearm at the frequency f The frequency f is within a range of 100 Hz to 200 Hz. The oscillation sensor 4 detects oscillations transmitted through the radial artery and converts them into an electrical signal. The amplifier 5 amplifies the output from the oscillation sensor 4 and provides it to the A/D converter 6. The A/D converter 6 converts the input into a digital signal and outputs it to the processor 7. The processor 7 performs a phase detection to determine a change in phase, as viewed from the center of an arc distribution, which indicates a change in velocity of propagation of the oscillations corresponding to a change in blood pressure. This change is calibrated by values of systolic and diastolic pressures measured through the cuff 8 and the blood pressure measuring device 9 to determine the blood pressure continuously. The waveform of the change is indicated on the display 10. The dc power supply 11 is connected to an ac power supply (not shown) through the plug 12 and provides a dc constant voltage to each block.

It is important for precise measurement of the blood pressure in the above system to detect weal oscillation transmitted through the blood vessel with high sensitivity. The power spectrum of a digital signal into which an output of the oscillation sensor 4 amplified by the amplifier 5 is converted by the A/D converter 6 when the exciter 2 is at rest is shown in FIG. 4 which represents the spectrum of noises added to the system. A frequency component within a range b is a patient's pulse component.

FIG. 4 shows that the power of noise rises at each of integral multiples of the frequency fs of the ac power supply. This is caused by the fundamental and harmonics of an output from the ac power supply entering the input of the system, which will compromise the sensitivity of detection of the oscillation extremely.

The frequency fs of an output from the ac power supply to the dc power supply 11 is different between used devices or countries. It is, thus, difficult to specify the frequency fs in advance.

The frequencies fd1 and fd2 in FIG. 4 are also equivalent to those of vibrations or electromagnetic noises produced by equipment used together with a blood pressure measuring system of the above type in, for example, an operating room that are factors of decreasing the sensitivity of detection of the oscillation. It is difficult to specify the frequency of the noises in advance because peripheral devices used along with the blood pressure measuring system are changed depending upon operating environments.

SUMMARY OF THE INVENTION

It is therefore a principal object of the present invention to avoid the disadvantages of the prior art.

It is another object of the present invention to provide a blood pressure determining system designed to measure the blood pressure accurately regardless of electric noises arising from an ac power supply and/or other peripheral devices.

According to one aspect of the invention, there is provided a blood pressure determining apparatus which comprises: (a) an exciter applying oscillations to a blood vessel of a subject; (b) an oscillation sensor monitoring the oscillations propagated through the blood vessel to provide an electric signal indicative thereof; (c) a signal processor including a blood pressure determining circuit determining a blood pressure of the subject based on the signal from said oscillation sensor; (d) a signal analyzer analyzing a frequency of the signal from said oscillation sensor to provide a signal indicative thereof; and (e) a frequency controller controlling a frequency of oscillations to be produced by said exciter based on the signal from said signal analyzer.

In the preferred mode of the invention, said signal analyzer analyzes the frequency of the signal which is outputted from said oscillation sensor when said exciter is in an off-state to determine a small noise frequency band in which a power of electric noise is small. The frequency controller sets the frequency of oscillations to be produced by said exciter to any value of the small noise frequency band.

The signal processor may alternatively define a plurality of frequency ranges in the small noise frequency band and performs a text to apply oscillations to the subject at a frequency that is a central one of each of the frequency ranges to select one of the central frequencies which allows a waveform of the blood pressure in the outputs of the oscillation sensor to be detected with the best sensitivity as the frequency of oscillations to be produced by said exciter.

According to another aspect of the invention, there is provided a method of determining a frequency of oscillations to be applied through an exciter in a blood pressure determining apparatus to a blood vessel of a subject to monitor a frequency of the oscillations propagated through the blood vessel to monitor an output of an oscillation sensor for determining a blood pressure of the subject continuously and non-invasibly, which comprises the steps of: (a) monitoring an output of the oscillation sensor when the exciter applies no oscillation to the subject to determine a power spectrum of noise signals contained in the output; and (b) setting the frequency of oscillations to be applied to the blood vessel of the subject through the exciter to a value within a band of the power spectrum in which a power of noise is small. This enables the output of the oscillation sensor to be provided without any electric disturbances.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
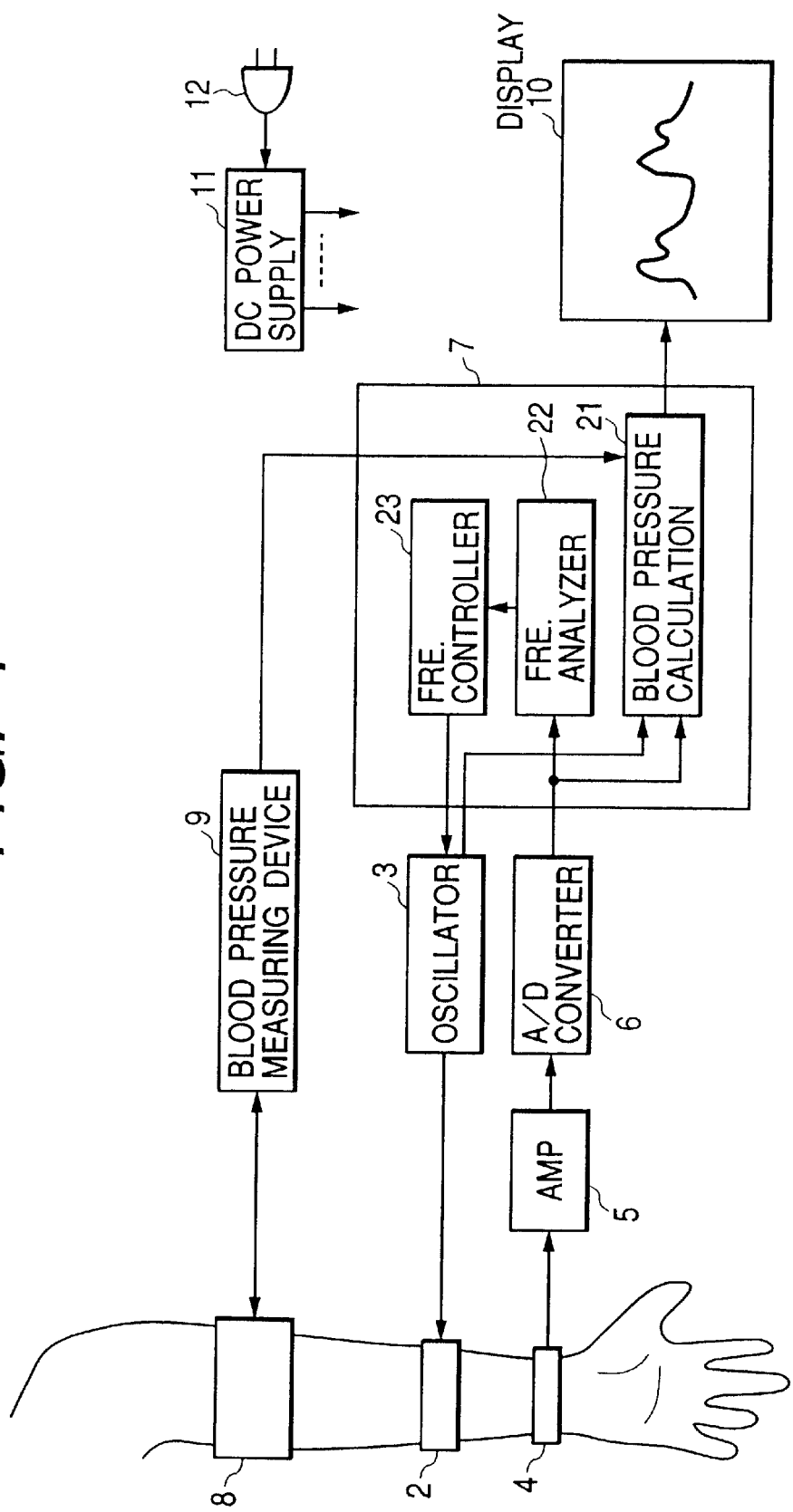
FIG. 1 a block diagram which shows a blood pressure determining apparatus of the invention.

Referring now to the drawings, wherein like numbers refer to like parts in several views, particularly to FIG. 1, there is shown a blood pressure determining apparatus according to the first embodiment of the invention which is designed to select a smaller noise power band from the power spectrum of an input signal when no oscillation is applied to the blood vessel and set the frequency of oscillations to within the selected band for eliminating the adverse effects of external noises on signal detection.

Figure 3:
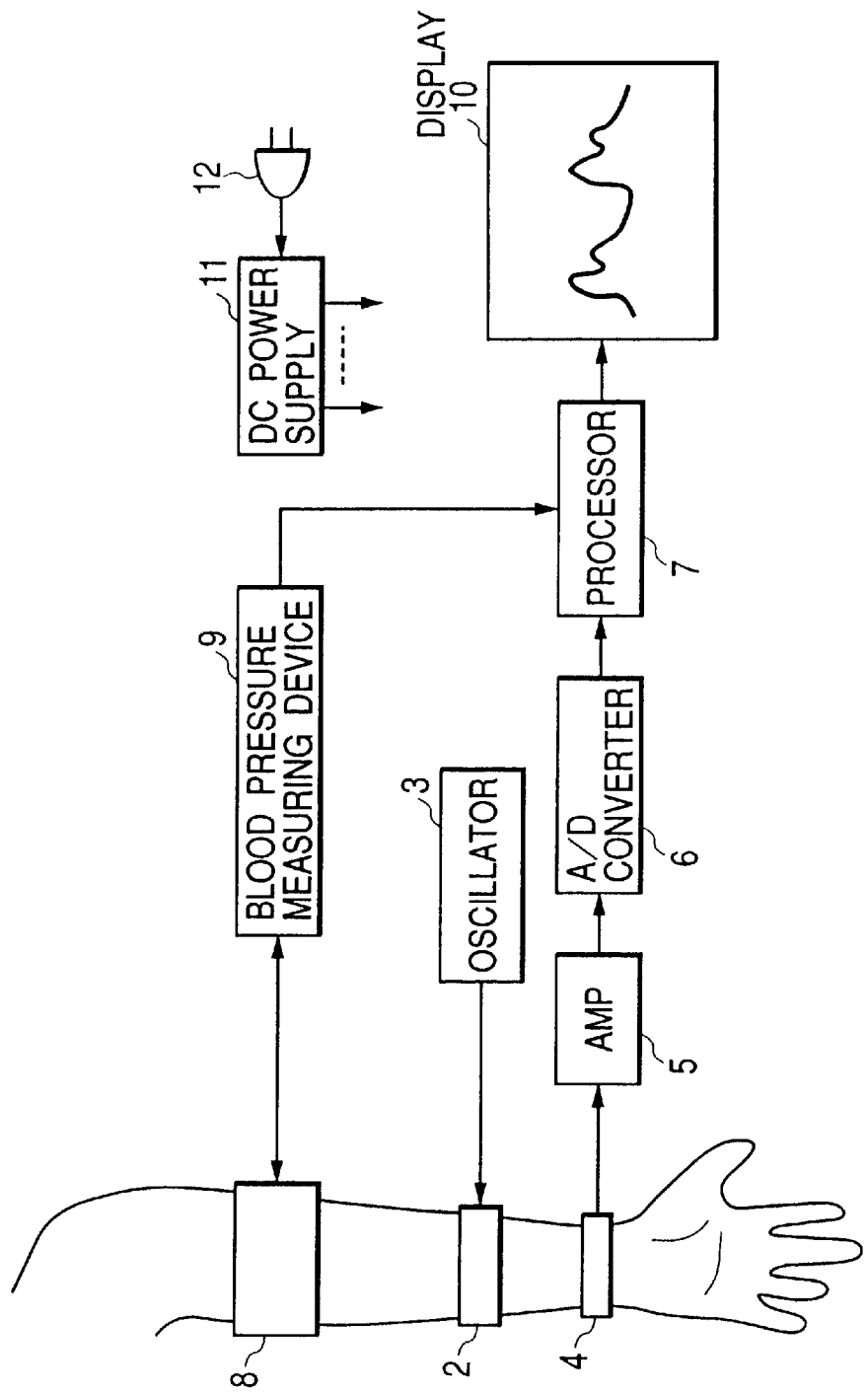
FIG. 3 is a block diagram which shows a conventional blood pressure determining apparatus.

The blood pressure determining apparatus of this embodiment includes generally an exciter 2, an oscillator 3, an oscillation sensor 4, an amplifier 5, an A/D converter 6, a processor 7, a cuff 8, a blood pressure measuring device 9, a display 10, and a dc power supply 11. The same reference numbers as employed in FIG. 3 refer to the same parts, and explanation thereof in detail will be omitted here. The structure in FIG. 3 is, as already discussed, taught in U.S. Pat. No. 5,590,649 issued on Jan. 7, 1997 disclosure of which is incorporated herein by reference.

The processor 7 includes a blood pressure calculating circuit 21 performing a blood pressure determining operation similar to that taught in U.S. Pat. No. 5,590,649, a frequency analyzer 22, and a frequency controller 23. The frequency analyzer 22 receives an output of the A/D converter 6 to determine the power spectrum thereof and provides a signal indicative thereof to the frequency controller 23. The frequency controller 23 determines an excitation frequency or frequency of oscillations to be produced by the exciter 2 as a function of the power spectrum determined by the frequency analyzer 22 and provides a signal indicative thereof to the oscillator 3. The output of the frequency controller 23 is also sent to the blood pressure calculating circuit 21.

Figure 4:
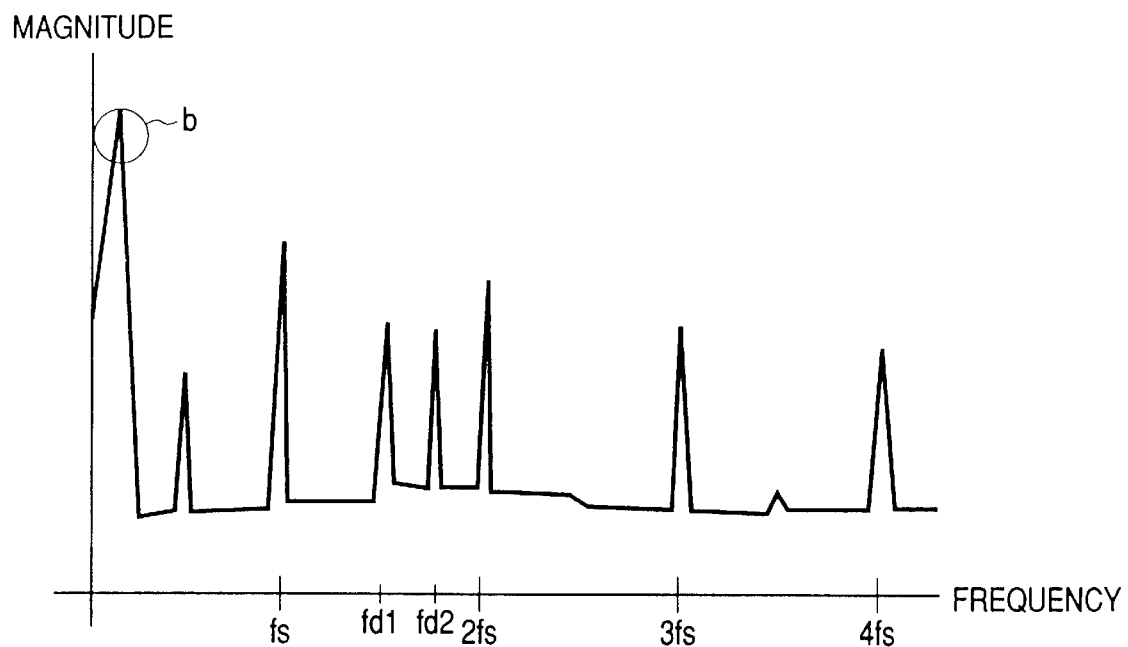
FIG. 4 is a graph which shows an example of the power spectrum of an output of an oscillation sensor.

When the blood pressure is determined, the oscillation sensor 4 and the exciter 2 are first attached to the patient. The processor 7 monitors an output of the oscillation sensor 4 through the amplifier 5 and the A/D converter 6 without activating the exciter 2. The frequency analyzer 22 of the processor 7 performs a Fast Fourier Transform (FFT) on the output of the oscillation sensor 4 to determine the power spectrum thereof, as shown in FIG. 4 as an example, and outputs a signal indicative thereof to the frequency controller 23.

The frequency controller 23 is responsive to the signal from the frequency analyzer 22 to select a band in which the power of noises is smaller, that is, which does not include noise components arising from peripheral devices, from the power spectrum of the sensor output when the exciter 2 is in off-state and sets the frequency of oscillations to be applied to the patient to any value within that band. Referring to the example in FIG. 4, the frequency controller 23 selects one of frequency ranges of fs to fd1 and 2fs to 3fs and determines the frequency of oscillations in the selected range. For instance, the frequency controller 23 selects a wider one of the frequency ranges of fs to fd1 and 2fs to 3fs or alternatively sets frequencies of oscillations in both the frequency ranges of fs to fd1 and 2fs to 3fs and selects one of the frequencies which can be measured at a higher sensitivity level.

The oscillator 3 produces a sine wave having the frequency specified by the frequency controller 23 and outputs it to the exciter 2. The exciter 2 oscillates the arm of the patient in the form of the sine wave. The oscillations applied to the patient are propagated through the blood vessel and monitored by the oscillation sensor 4. The oscillation sensor 4 converts the oscillations into an electric signal and provides it to the blood pressure calculating circuit 21 through the amplifier 5 and the A/D converter 6. The blood pressure calculating circuit 21 also receives the output from the oscillator 3 and uses it as a reference signal for the phase detection. The blood pressure calculating circuit 21 determines a change in phase of an output signal produced by the phase detection and calibrates it using values of the systolic and diastolic pressures measured through the cuff 8 to determine the patient's blood pressure continuously. The determined blood pressure is indicated on the display 10.

The blood pressure determining apparatus of the second embodiment will be discussed below which is designed to find the power spectrum of noise signals from an output of the oscillation sensor 4 when the exciter 2 is in the off-state and set the frequency of oscillations produced by the exciter 2 to any value within one of smaller noise bands which enables the waveform of the blood pressure to be detected with the best sensitivity.

Figure 2:
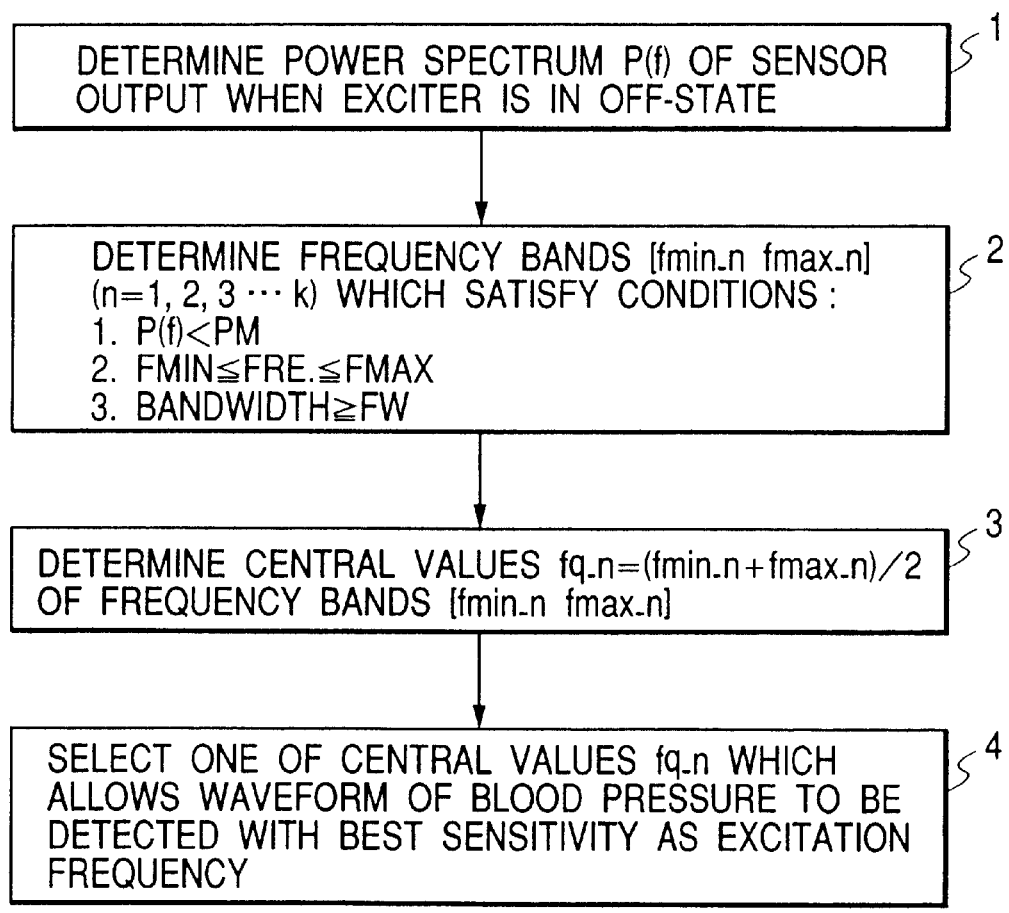
FIG. 2 is a flowchart of a program performed to determine the frequency of oscillations to be applied to a subject according to the second embodiment of the invention.

FIG. 2 shows a flowchart of a program performed by the processor 7 to determine the frequency of oscillations applied by the exciter 2 to the patient.

After entering the program, the routine proceeds to step 1 wherein an output from the oscillation sensor 4 when the exciter 2 is in the off-state is analyzed in frequency to determine the power spectrum P(f).

The routine proceeds to step 2 wherein frequency bands [fmin_n fmax_n] (n=1, 2, . . . k) are determined each of which satisfies the following conditions:

(1) the value of P(f) is smaller than a set value PM,
(2) the frequency is greater than a set value FMIN and smaller than FMAX, and
(3) the bandwidth is greater than a set value FW.

where the set value PM is so determined in terms of a signal-to-noise ratio of the apparatus that it may be possible to determine the blood pressure with sufficient accuracy within a band in which the noise power is less than the set value PM. If the frequency bands [fmin_n fmax_n] are not determined in the first program cycle, the set value PM is incremented, and the step 2 is performed again.

The set values FMIN and FMAX are upper and lower frequency limits of a band in which oscillations having a power required for blood pressure measurement are allowed to be propagated through the blood vessel and determined based on frequency bands used in the exciter 2 and detectable by the oscillation sensor 4 and blood vessel propagation characteristics. For example, the set value FMIN is on the order of 200 to 500 Hz. The set value FMAX is on the order of 1000 to 2000 Hz. The set value FW indicates a frequency band required for the blood pressure measurement and is preferably on the order of 20 to 100 Hz.

The routine proceeds to step 3 wherein the central value $fq\_n=(fmin\_n+fmax\_n)/2 (n=1, 2 \ldots k)$ of each of the frequency bands [fmin_n fmax_n] is determined.

The routine proceeds to step 4 wherein a blood pressure measurement text is performed to apply oscillations to the patient at the central frequency fq_n in each of the frequency bands [fmin_n fmax_n]. The processor 7 monitors outputs from the oscillation sensor 4 to select one fq_ ($1 \leq j \leq k$) of all the frequencies fq_n determined in step 3 which allows the waveform of the blood pressure to be detected at the best sensitivity level and sets the frequency fq_j to the frequency of oscillations to be produced by the exciter 4 for practical blood pressure measurement. For instance, the processor 7 selects one of all the frequencies fq_n which provides an arc distribution of data on phase detection having a greater radius or closer to the circularity (i.e., smaller dispersion of radii from the arc center).

The second embodiment, as apparent from the above discussion, enables the frequency of oscillations outputted by the exciter 2 to be selected which is most suitable for each patient without influence of any electric disturbances.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A blood pressure determining apparatus comprising:
    an exciter applying oscillations to a blood vessel of a subject;
    an oscillation sensor monitoring the oscillations propagated through the blood vessel to provide an electric signal indicative thereof;
    a signal processor including a blood pressure determining circuit determining a blood pressure of the subject based on the signal from said oscillation sensor;
    a signal analyzer analyzing a frequency of the signal from said oscillation sensor to provide a signal indicative thereof; and
    a frequency controller controlling a frequency of oscillations to be produced by said exciter based on the signal from said signal analyzer.

2. A blood pressure determining apparatus as set forth in claim 1, wherein said signal analyzer analyzes the frequency of the signal which is outputted from said oscillation sensor when said exciter is in an off-state to determine a small noise frequency band in which a power of electric noise is small, and said frequency controller sets the frequency of oscillations to be produced by said exciter to any value of the small noise frequency band.

3. A blood pressure determining apparatus as set forth in claim 1, wherein said signal analyzer analyzes the frequency of the signal which is outputted from said oscillation sensor when said exciter is in an off-state to determine a small noise frequency band, and said signal processor defines a plurality of frequency ranges in the small noise frequency band and performs a text to apply oscillations to the subject at a frequency that is a central one of each of the frequency ranges to select one of the central frequencies which allows a waveform of the blood pressure in outputs of the oscillation sensor to be detected with the best sensitivity as the frequency of oscillations to be produced by said exciter.

4. A method of determining a frequency of oscillations to be applied through an exciter in a blood pressure determining apparatus to a blood vessel of a subject to monitor a frequency of the oscillations propagated through the blood vessel to monitor an output of an oscillation sensor for determining a blood pressure of the subject continuously and non-invasibly, comprising the steps of:
    monitoring an output of the oscillation sensor when the exciter applies no oscillation to the subject to determine a power spectrum of noise signals contained in the output; and
    setting the frequency of oscillations to be applied to the blood vessel of the subject through the exciter to a value within a band of the power spectrum in which a power of noise is small.

* * * * *